United States Patent
Maini et al.

(12) 
(10) Patent No.: US 6,368,347 B1
(45) Date of Patent: Apr. 9, 2002

(54) EXPANDED POLYTETRAFLUOROETHYLENE VASCULAR GRAFT WITH COATING

(75) Inventors: Roshan Maini, Bridge of Weir; Karen Kelso, Kilmarnock, both of (GB)

(73) Assignee: Sulzer Vascutek Ltd., GB-Renfrewshire (GB)

( * ) Notice: Subject to any disclaimer, the term of this patent is extended or adjusted under 35 U.S.C. 154(b) by 0 days.

(21) Appl. No.: 09/298,296

(22) Filed: Apr. 23, 1999

(51) Int. Cl.[7] .................................................. A61F 2/06

(52) U.S. Cl. ...................... 623/1.46; 623/1.47; 623/1.48

(58) Field of Search ............................... 623/1.38, 1.39, 623/1.44–1.54

(56) References Cited

U.S. PATENT DOCUMENTS

| | | | |
|---|---|---|---|
| 3,272,204 A | * | 9/1966 | Artandi et al. ............... 128/334 |
| 4,193,138 A | | 3/1980 | Okita .............................. 3/1.4 |
| 4,747,848 A | * | 5/1988 | Maini ............................. 623/1 |
| 4,842,575 A | * | 6/1989 | Hoffman, Jr. et al. ........ 600/36 |
| 5,665,114 A | | 9/1997 | Weadock et al. .............. 623/1 |
| 5,851,229 A | * | 12/1998 | Lentz et al. .................. 623/1 |

* cited by examiner

*Primary Examiner*—Corrine McDermott
*Assistant Examiner*—Hieu Phan
(74) *Attorney, Agent, or Firm*—Kenneth S. Barrow

(57) ABSTRACT

A vascular graft comprised of a tubular polytetrafluoroethylene (ePTFE) sheet. The ePTFE sheet has a substantially uniform coating of bioresorbable gel material on an outer surface. The coating minimizes bleeding through suture holes in the ePTFE sheet and an increase in longitudinal extensibility.

11 Claims, 1 Drawing Sheet

EXPANDED POLYTETRAFLUOROETHYLENE VASCULAR GRAFT WITH COATING

BACKGROUND OF THE INVENTION

1. Field of the Invention

This invention relates to vascular prostheses of polytetrafluoroethylene.

2. Description of the Prior Art

Vascular prostheses made of knitted or woven fabric of a polyester (e.g. Dacron polyester, a trademark of E.I du Pont de Nemours & Co., Inc.) or of sheets of polytetrafluoroethylene are currently available, or have been described in the art. Expanded polytetrafluoroethylene (ePTFE) tubes have a microporous structure consisting of small nodes interconnected with many tiny fibrilla. EPTFE is extruded into tubes to make vascular grafts. Although vascular grafts constructed using such material are generally clinically successful, there is a tendency to leak blood at suture holes where the graft is attached to a patient. Because of the generally non-resilient characteristics of ePTFE material, suture needles create a larger hole in the sheet than the suture. There is a tendency for blood to leak around the sutures. Intraoperative measures taken to reduce or eliminate bleeding prolong operation times and are clearly undesirable. Such measures may include compression or other physical intervention.

Previous solutions to the problem of suture hole leakage have relied on filling the porous structure of the ePTFE material with a bioresorbable sealant. For example, Okita, U.S. Pat. No. 4,193,138, proposed introducing a water-soluble polymer into the pores of the ePTFE material and then treating the polymer to render it water-insoluble. Weadock et al., U.S. Pat. No. 5,665,114, proposed filling the pores with solid biocompatible material of natural origin. A water-soluble substance is introduced into the pores and treated to render it water-insoluble.

In connection with grafts made with knitted or woven fabrics, materials such as collagen or gelatin have been applied to the highly porous surface of such textiles. See, for example, U.S. Pat. Nos. 3,272,204; 4,747,848; 4,842,575 or 5,197,977. The materials can be expected to penetrate into the voids produced by the woven or knitted structure of the fabric and thus reduce blood leakage throughout the entire fabric, as well as at locations where sutures pass through the fabric. Of course, since fibers of the fabric will spread apart to allow passage of the suture needle and then return to a closer configuration adjacent a suture, the problem of suture hole leakage in fabric grafts is not as severe as in ePTFE grafts.

SUMMARY OF THE INVENTION

The prosthesis of our invention seeks to overcome the limitations of the prior art by providing an ePTFE vascular graft having a substantially uniform coating of bioresorbable gel on an outer surface. The method of application causes the coating to be confined substantially entirely to the outer surface, meaning that there is minimal penetration of the coating into the pores of the ePTFE material. Preferably, the bioresorbable gel is plasticised with glycerol.

DETAILED DESCRIPTION OF PREFERRED EMBODIMENTS

Preferred embodiments of the invention are described below. In the Figures and in this description, like numerals will be used to refer to like parts.

Figure 1:
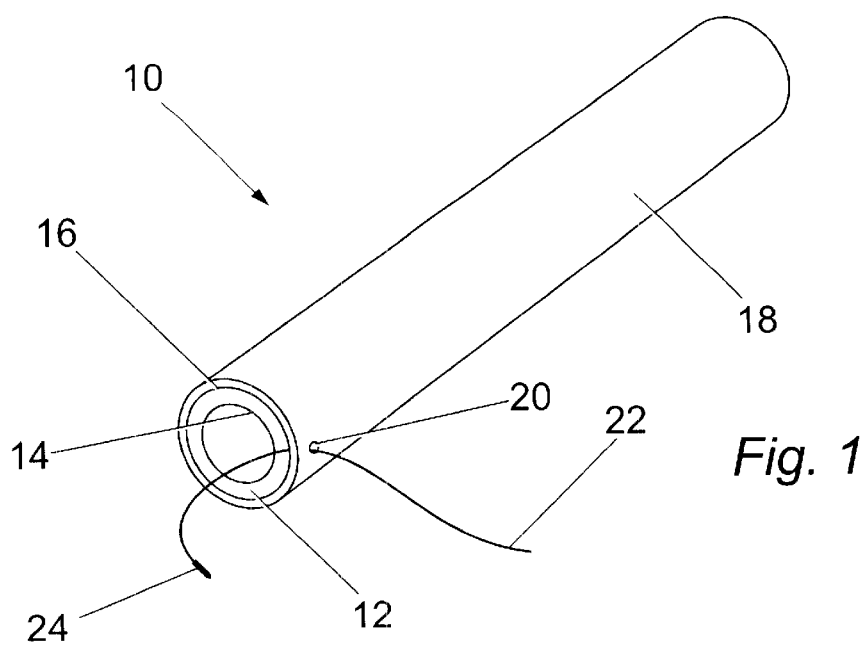
FIG. 1 is a perspective view of a tubular vascular prosthesis.

FIG. 1 illustrates a tubular vascular graft 10. The vascular graft 10 is comprised of a tube of ePTFE material 12 having an inside surface 14 and an outside surface 16. The inside surface 14 is expected to be adjacent a flow of blood when the graft is implanted in the body of a patient. The outside surface 16 is covered with a gel coating 18. Preferably, the coating 18 is confined to the surface only, and does not penetrate significantly into voids in the ePTFE material.

Figure 2:
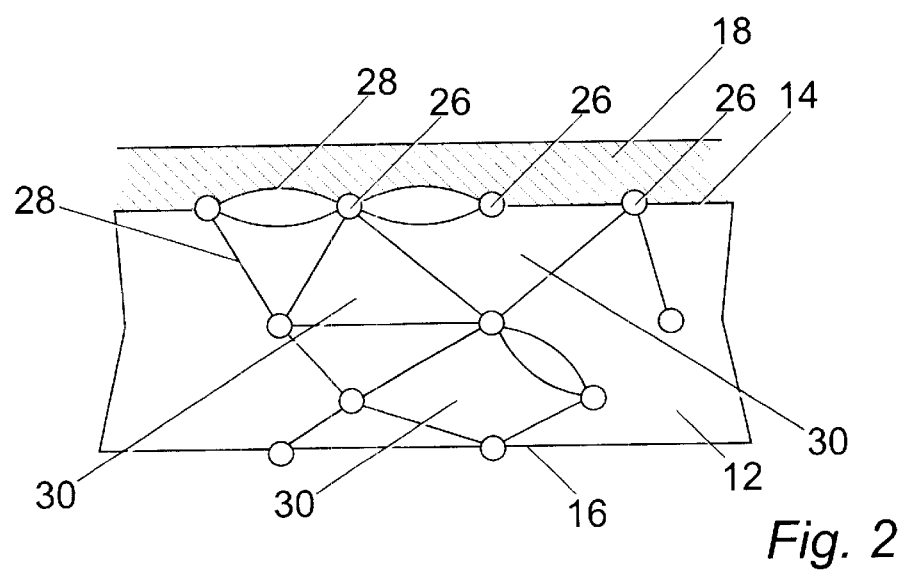
FIG. 2 is a cross-sectional view of a layer of ePTFE material with a gelatin coating.

As illustrated in FIG. 2, the ePTFE material 12 is comprised of a plurality of nodes 26, interconnected by fibrils 28. This structure forms voids or pores 30 between the fibrils. Those skilled in the art recognize that the character of the fibrils and voids can be modified by various treatments. Whatever the selected size of the voids, however, the gel coating 18 remains essentially entirely on the outer surface 14 of the sheet 12. It is thought that this structure will enhance the flexibility of the graft 10, while providing sealing around sutures.

Figure 3:
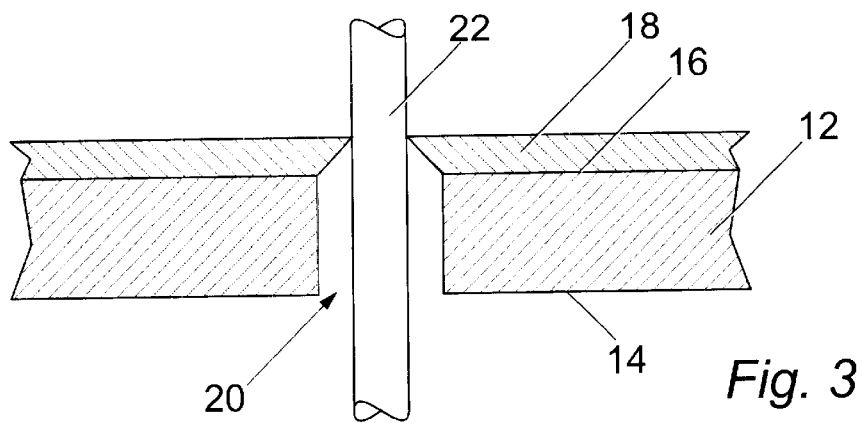
FIG. 3 is a cross-sectional view of the ePTFE material of FIG. 2, illustrating a suture passing through a hole created by a suture needle.

In use, it is contemplated that the graft 10 will be sutured in place within the body of a patient. A suture needle 24 having an attached suture 22 is passed through the ePTFE material 12 and the gel coating 18, producing a suture hole 20. As can be seen in FIG. 3, the needle produces a hole 20 which is wider than the suture 22. Because of the properties of the ePTFE material 12, the material 12 does not collapse elastically around the suture. This can lead to leakage of blood around the suture. In my invention, however, the gel coating 18 collapses radially around the suture, and closes the suture hole while healing takes place.

The gel coating 18 is preferably a bioresorbable gelatin. A suitable gelatin is a mammalian gelatin, described in U.S. Pat. No. 4,747,848, which is incorporated herein by reference. Such gelatin comprises a mixture of 50% normal limed bone gelatin and 50% normal gelatin treated with chloride of succinic acid.

Other gels may also be used such as a polysaccharide gel such as Dextran™ gel.

Alternatively, other appropriate synthetic and biological hydrogel may be used. The preparations of such hydrogels are known in the art. Synthetic hydrogels may include poly (2-hydroxyethyl methacrylate) [PHEMA]; poly (vinyl alcohol) [PVA]; poly (ethylene oxide) [PEO]; poly (carboxylic acids); poly(N-vinyl 2-pyrollidene) [PVP] or other synthetic hydrophilic polymers. Biological hydrogels may include starches algenates celluloces agars, chitosan, collagen gels and the like.

EXAMPLE 1

A 10% solution of gelatin using 1 part limed bone and 1 part succinylated gelatin was prepared daily and maintained at a constant temperature of 37° C. in an oven until used. To produce succinylated gelatin, limed bone gelatin is treated with chloride of succinic acid. Lengths of ePTFE tube were fitted securely on a mandrel. Each end of the graft was cable tied to secure the ePTFE tube for coating.

The gelatin solution was then poured into a vertical container on a hot plate. The temperature of the gelatin was maintained between 35 and 40° C. to ensure the solution did not set during use. A second vertical container with isopropanol was also prepared and the mandrel, with graft, placed into this second container for 1 minute. Excess isopropanol was removed and the mandrel was placed immediately into the gelatin solution for approximately 10 seconds. The isopropan bath prepares the exterior, hydrophobic surface of the ePTFE material to receive the gelatin by wetting the exterior surface. The mandrel was manually rotated in the gelatin solution to ensure complete coverage of the ePTFE tube. On removal the gelatin was manually massaged along the length of the tube while being rotated in front of a cold air fan. This procedure was performed immediately upon removal of the ePTFE graft from the gelatin solution. Massage was stopped as soon as the gelatin began to feel tacky. Excess manual action led to non-uniformity and peeling of the coating. The mandrel, with graft, was left in front of a cold blowing fan to dry completely before applying a second coating. After application of a final third coating, the graft was left to dry for 1 hour until hard. After drying, the graft as detached from the cable ties and the coated graft removed from the mandrel. A third vertical container with 50% solution of formaldehyde was also prepared and the coated graft placed in this solution overnight to induce cross-linking.

The coated PTFE graft was removed after cross-linking and washed for a minimum of 5 hours before being plasticised. For this process an 80% glycerol solution was prepared and heated to 65° C. in a water bath. Coated grafts were placed in this solution for 30 minutes until they felt soft and flexible. The grafts were removed from the glycerol solution for final wash. Final washing involved submersion for 15 minutes in isopropanol at 125 rpm to remove excess glycerol. PTFE grafts were finally air dried with a fan. Before final sterilization and packaging, coated ePTFE grafts were gently extended manually from their coated compressed state to aid flexibility and extendibility.

EXAMPLE 2

A 15% solution of gelatin was prepared daily and maintained at a constant temperature of 37° C. in an oven until used. Lengths of ePTFE tube were fitted securely on a mandrel. Each end of the graft was cable tied to secure the ePTFE tube for coating.

The gelatin solution was then poured into a vertical container on a hot plate. The temperature of the gelatin solution was maintained between 35 and 40° C. to ensure the solution did not set during use. A second vertical container with isopropanol was also prepared and the mandrel, with graft, was placed into this second container for 1 minute. Excess isopropanol was removed and the mandrel was placed immediately into the gelatin solution for approximately 15 seconds. During this time the mandrel was manually rotated to ensure complete coverage of the ePTFE tube. On removal the gelatin was manually massaged along the length of the tube while being rotated in from of a cold air fan. This procedure was performed immediately upon removal of the ePTFE graft from the gelatin solution. Massage was stopped as soon as the gelatin began to feel tacky. Excess manual action led to non-uniformity and peeling of the coating. The mandrel, with graft, was left in front of a cold blowing fan to dry completely before applying a second coating. After application of a final third coating, the graft was left to dry for 1 hour until hard. After drying, the graft as detached from the cable ties and the coated graft was removed from the mandrel. A third vertical container containing a 50% solution of formaldehyde was also prepared and the coated graft placed in this solution overnight to induce cross-linking.

The coated PTFE graft was removed after cross-linking and washed for a minimum of 5 hours before being plasticised. For this process an 80% glycerol solution was prepared and heated to 70° C. in a water bath. Coated grafts were placed in this solution for 30 minutes until they felt soft and flexible. The grafts were removed from the glycerol solution for final wash. Final washing involved submersion for 15 minutes in isopropanol at 125rpm to remove excess glycerol. PTFE grafts were finally air dried with a fan. Before final sterilization and packaging, coated ePTFE grafts were gently extended manually from their coated compressed state to aid flexibility and extendibility.

Expanded polytetrafluoroethylene vascular grafts treated according to the described techniques display an unexpectedly increased longitudinal extensibility over uncoated grafts. Longitudinal extensibility is desirable for reducing the need for precise length adjustment during implantation. In general, past treatments to increase the stretchableness of ePTFE grafts have employed thermal treatments which modify the node/fibril structure of the grafts. The grafts according to our invention provide increased longitudinal extensibility without altering the node/fibril structure of the graft.

The improved characteristics of the graft were tested using an elongation test. In this test, the lengths of uncoated and coated vascular grafts were measured. One end of the grafts was secured and selected weights were suspended from the opposite end. The elongated length was measured and the per cent increase in length was calculated. The weights were removed from the coated grafts and the grafts were allowed to return to an unloaded length after elongation. The unloaded length after elongation was measured and the selected weights were re-applied. A second elongated length was measured and the per cent increase of the second elongated length over the unloaded length after elongation was calculated. The results observed are recorded in the following Table 1.

TABLE 1

| | Percent Increase in Length | | |
|---|---|---|---|
| Weights Applied (g) | Uncoated | Coated | Coated, after Elongation |
| 125 | 2 | 13 | 7 |
| 250 | 4 | 16 | 15 |
| 500 | 4 | 24 | 20 |
| 1000 | 4 | 28 | 27 |

From the foregoing description it should be apparent that the present invention provides an ePTFE vascular graft with a substantially uniform coating of a bioresorbable gel on an outer surface. Further it will be apparent that various changes may be made in the form of the elements thereof without departing from the spirit and scope of the invention, the form and examples hereinbefore described being merely exemplary embodiments. Therefore, it is intended that the scope of the invention be determined by the appended claims or their equivalents.

What is claimed is:

1. An implantable vascular graft comprising
   an expanded polytetrafluoroethylene substrate, said substrate having a wall structure with an inside wall and an outside wall and including nodes and fibrils with pores present between said nodes and said fibrils, and a layer of resilient, bioresorbable material on at least one wall of said substrate, said material being substantially excluded from said pores.

2. The implantable vascular graft according to claim 1 wherein the resilient bioresorbable material is a gel.

3. The implantable vascular graft according to claim 2 wherein said gel comprises of succinylated gelatin.

4. The implantable vascular graft according to claim 2 wherein said gel is plastized with glycerol.

5. The implantable vascular graft according to claim 1 wherein said resilient bioresorbable material is comprised of polysaccharide.

6. The implantable vascular graft according to claim 1 wherein said resilient bioresorbable material is comprised of a hydrogel.

7. The implantable vascular graft of claim 1 wherein said layer is on said outside wall.

8. An implantable vascular graft comprising
   an expanded polytetrafluoroethylene substrate, said substrate having a wall structure with an inside wall and an outside wall and including nodes and fibrils with pores present between said nodes and said fibrils, and
   a layer of resilient, bioresorbable material gel entirely on said outer wall of said substrate, said material being excluded from said pores.

9. The implantable vascular graft of claim 8 wherein said layer comprises a plurality of coatings of gel applied one above another above said outer wall of said substrate.

10. The implantable vascular graft of claim 9 wherein said coatings have been cross-linked.

11. An implantable vascular graft comprising
    an expanded polytetrafluoroethylene substrate, said substrate having a wall structure with an inside wall and an outside wall and including nodes and fibrils with pores present between said nodes and said fibrils, and
    a layer of resilient, bioresorbable gel solely on at least one wall of said substrate, said vascular graft being substantially more longitudinally resiliently extensible than said expanded polytetrafluoroethylene substrate alone.

* * * * *